(12) United States Patent
Spears et al.

(10) Patent No.: US 7,919,322 B2
(45) Date of Patent: Apr. 5, 2011

(54) TARGETED DELETIONS USING RETROELEMENT-MEDIATED PLACEMENT OF RECOMBINATION SITES

(75) Inventors: Melissa Spears, St. Louis, MO (US); Greg Davis, Webster Groves, MO (US); Kevin Kayser, Chesterfield, MO (US)

(73) Assignee: Sigma-Aldrich Co., St. Louis, MO (US)

( * ) Notice: Subject to any disclaimer, the term of this patent is extended or adjusted under 35 U.S.C. 154(b) by 735 days.

(21) Appl. No.: 11/391,972

(22) Filed: Mar. 29, 2006

(65) Prior Publication Data

US 2007/0231865 A1 Oct. 4, 2007

(51) Int. Cl.
C12N 15/74 (2006.01)
C12N 15/63 (2006.01)
C12N 15/64 (2006.01)
C12N 15/65 (2006.01)
C12N 15/00 (2006.01)
C12P 21/00 (2006.01)

(52) U.S. Cl. ...... 435/471; 435/478; 435/69.1; 435/71.1; 536/23.71; 536/23.72; 536/25.32

(58) Field of Classification Search .................. None
See application file for complete search history.

(56) References Cited

U.S. PATENT DOCUMENTS

| 4,959,317 | A | * | 9/1990 | Sauer ........................... 435/462 |
| 5,698,421 | A | | 12/1997 | Lambowitz et al. |
| 5,804,418 | A | | 9/1998 | Lambowitz et al. |
| 5,869,634 | A | | 2/1999 | Lambowitz et al. |
| 5,872,241 | A | | 2/1999 | Pyle et al. |
| 6,001,608 | A | | 12/1999 | Lambowitz et al. |
| 6,027,895 | A | | 2/2000 | Lambowitz et al. |
| 6,140,129 | A | | 10/2000 | Cox et al. |
| 6,306,596 | B1 | | 10/2001 | Lambowitz et al. |
| 2004/0132145 | A1 | * | 7/2004 | Park et al. ..................... 435/106 |

OTHER PUBLICATIONS

Cousineau et al, Retrohoming of a Bacterial Group II Intron: Mobility via Complete Reverse Splicing, Independent of Homologous DNA Recombination, Cell, Vol. 94, 451-462, Aug. 21, 1998.*
Hajdukiewicz et al, Multiple pathways for Cre/lox-mediated recombination in plastids, The Plant Journal (2001) 27(2), 161-170.*
Karberg et al, Group II introns as controllable gene targeting vectors for genetic manipluation of bacteria, Nature Biotechnology, 2001, vol. 19, pp. 1162-1167.*

Mastroianni et al, Group II Intron-Based Gene Targeting Reactions in Eukaryotes, PLoS One, 2008, vol. 3 (9), pp. 1-15.*
Suzuki et al, Cre/loxP-mediated deletion system for large genome rearrangements in *Corynebacterium glutamicum*, Appl Microbiol Biotechnol (2005) 67: 225-233.*
Coros, C., et al., "Retrotransposition strategies of the *Lactococcus lactis* Ll.LtrB group II intron are dictated by host identity and cellular environment" (2005) *Mol Microbiol*, pp. 509-524, vol. 56.
Guo, H., et al., "Group II intron endonucleases use both RNA and protein subunits for recognition of specific sequences in double-stranded DNA" (1997) *EMBO J*, pp. 6835-6848, vol. 16, No. 22.
Guo, H., et al., "Group II Introns Designed to Insert into Therapeutically Relevant DNA Target Sites in Human Cells" (2000) *Science*, pp. 452-457, vol. 289.
Ichiyanagi, K., et al., "Retrotransposition of the Ll.LtrB group II intron proceeds predominantly via reverse splicing into DNA targets" (2002) *Mol Microbiol*, pp. 1259-1272, vol. 46.
Karberg, M., et al., "Group II introns as controllable gene targeting vectors for genetic manipulation of bacteria" (2001) *Nature Biotech*, pp. 1162-1167, vol. 19.
Perutka, J., et al., "Use of Computer-designed Group II Introns to Disrupt *Escherichia coli* DExH/D-box Protein and DNA Helicase Genes" (2004) *J Mol Biol*, pp. 421-439, vol. 336.
Suzuki, N., et al., "Large-Scale Engineering of the *Corynebacterium glutamicum* Genome" (2005) *App & Envir Microbiol*, pp. 3369-3372, vol. 71, No. 6.
Yang, J., et al., "Efficient integration of an intron RNA into double-stranded DNA by reverse splicing" (1996) *Nature*, pp. 332-335, vol. 381.
Yu, B.J., et al., "Minimization of the *Escherichia coli* genome using a Tn5-targeted Cre/*loxP* excision system" (2002) *Nature Biotech*, pp. 1018-1023, vol. 20.
Zhong, J., et al., "Targeted and random bacterial gene disruption using a group II intron (targetron) vector containing a retrotransposition-activated selectable marker" (2003) *Nucl Acids Res*, pp. 1656-1664, vol. 31, No. 6.
Zimmerly, S., et al., "Group II Intron Mobility Occurs by Target DNA-Primed Reverse Transcription" (1995) *Cell*, pp. 545-554, vol. 82.
Zimmerly, S., et al., "A Group II Intron RNA Is a Catalytic Component of a DNA Endonuclease Involved in Intron Mobility" (1995) *Cell*, pp. 529-538, vol. 83.

\* cited by examiner

*Primary Examiner* — Maria Marvich
(74) *Attorney, Agent, or Firm* — Polsinelli Shughart PC

(57) ABSTRACT

The present invention provides methods, nucleic acid constructs, and kits for selectively deleting a region of a nucleic acid sequence. Specifically, it utilizes retargeting retroelements to place site-specific recombination sites at targeted locations in the nucleic acid sequence. The region between the recombination sites is then deleted using a site-specific recombination system.

10 Claims, 7 Drawing Sheets

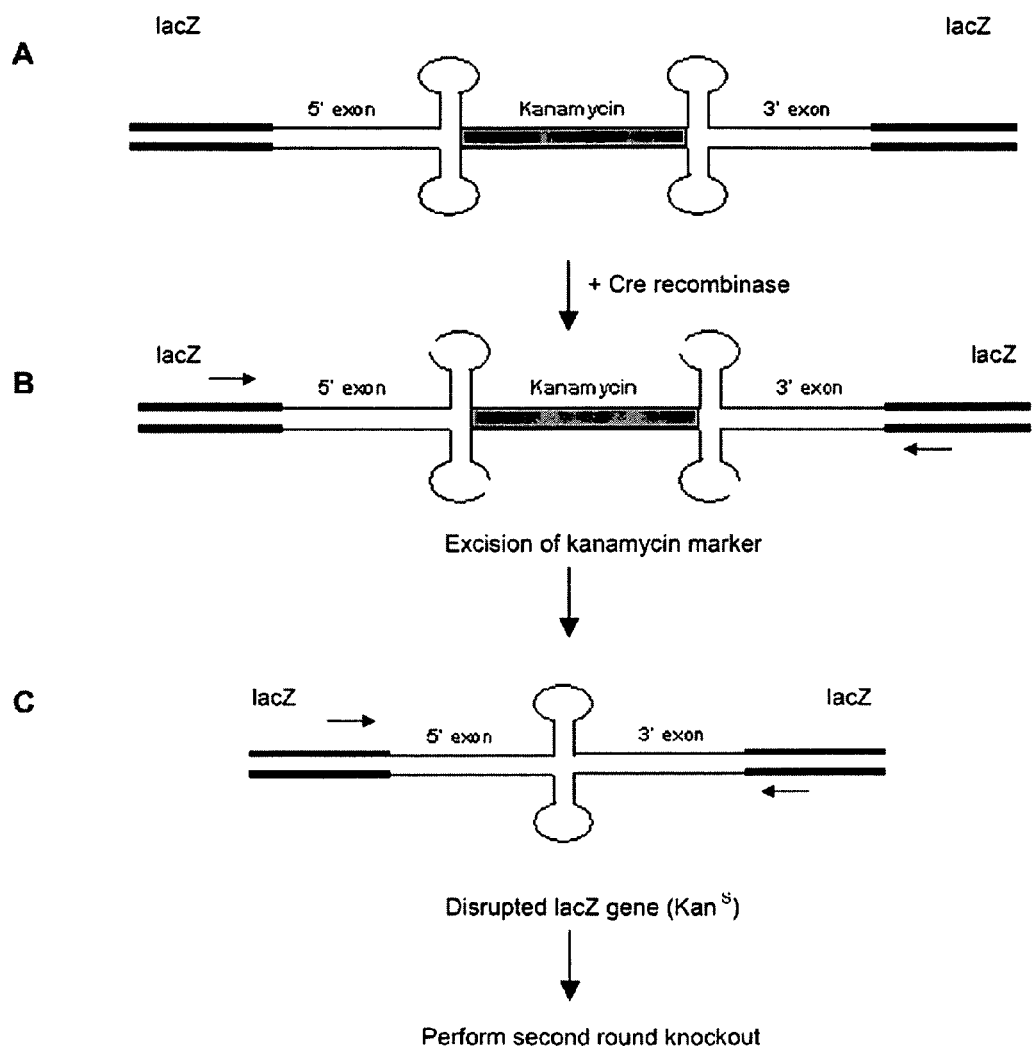

Figure 3 wt loxP site    ATAACTTCGTATAGCATACATTATACGAAGTTAT mutant loxP site  CTA-CTTCGTATAGCATACATTATACGAAGTTAT

| Quadrant | Strain | cyn operon genes deleted |
|---|---|---|
| 1 | wild-type BL21 (DE3) | none |
| 2 | Δ cynX 1077\|1078s-lacZ1063\|1064a | cynX* |
| 3 | Δ cynS 120\|121s-lacZ1063\|1064a | cynS*, X |
| 4 | Δ betT 603\|604s-lacZ1063\|1064a | cynT, S, X |

*denotes a partial deletion.

US 7,919,322 B2

TARGETED DELETIONS USING RETROELEMENT-MEDIATED PLACEMENT OF RECOMBINATION SITES

FIELD OF THE INVENTION

The present invention relates to nucleic acid constructs, methods, and kits for deleting a region of a nucleic acid sequence.

BACKGROUND OF THE INVENTION

The ability to manipulate and engineer genomic sequences has helped to elucidate basic biological processes, enhance the production of biochemicals and pharmaceuticals, and provide insight into clinically relevant disease states. The disruption or deletion of genes has been used to identify essential genes in a variety of organisms and to investigate the functions of unknown genes. While much has been learned from random deletions, it is desirable to target a specific gene or region of a chromosome for deletion. Commonly used methods for deleting genes or chromosomal regions include homologous recombination and site-specific recombination. Homologous recombination has the disadvantage that extensive regions of sequence similarity are required between the recombining DNA sequences. To date, deletion experiments using a site-specific recombination system (such as Cre/loxP and Flp/FRT) are cumbersome in that they require the construction of several customized targeting constructs or complex PCR experiments.

Attempts have been made to circumvent some of these difficulties. FRT recombination sites have been inserted permanently at random locations in the E. coli genome using a transposon (Tn5) (U.S. Pat. No. 6,140,129). Similarly, Tn5 transposons were used to insert loxP recombination sites at random locations in E. coli, and the region between the sites was deleted by expression of Cre recombinase (Yu et al. 2002, Nature Biotechnology 20, 1018-1023). Transposons insert at random locations in the DNA, however. Thus, transposon-mediated insertions of recombination sites do not permit precise or targeted deletions. In another attempt, loxP recombination sites were positioned at specific locations in the Corynebacterium glutamicum genome by homologous recombination using strain-specific island sequences (Suzuki et al. 2005, Applied Environmental Microbiol. 71, 3369-3372). This method is restricted for use in bacterial genomes, and in only those with strain-specific islands. A need exists, therefore, for a simple method to position site-specific recombination sites at targeted locations in a broad range of organisms, whereby the region between the recombination sites at the targeted locations may be deleted by a site-specific recombinase.

SUMMARY OF THE INVENTION

Among the several aspects of the invention is the provision of methods for selectively deleting a region of a nucleic acid sequence by 1) placing a recombination site at a first targeted location in the nucleic acid sequence using a first retargeted retroelement that carries at least one recombination site, 2) placing a recombination site at a second targeted location in the nucleic acid sequence using a second retargeted retroelement that carries at least one recombination site, and 3) using a site-specific recombination system to delete the region between the recombination sites at the first and second targeted locations.

Another aspect of the invention provides nucleic acid constructs comprising sequence encoding a retargeting group II intron, wherein at least one recombination site is inserted into the intron sequence. The group II intron may further comprise a retrotransposition-activated selectable marker (RAM). It was discovered during construction of the nucleic acid constructs that insertion of loxP sites into a group II intron did not affect the retargeting ability of the intron, whereas no mobility was observed when FRT sites flanked the kan-RAM marker.

An additional aspect of the invention encompasses kits for selectively deleting a region of a nucleic acid sequence. Minimally, a kit provides a nucleic acid construct comprising a retargeting group II intron sequence and at least one recombination site sequence, instructions for targeting and inserting the recombination sites into targeted locations in the nucleic acid sequence, and instructions for deleting the region between the recombination sites.

BRIEF DESCRIPTION OF THE DRAWINGS

FIG. 3 presents the sequences of the wild type loxP site (SEQ ID NO:1) and the deletion-substitution mutation (SEQ ID NO:2) present in the 5' loxP site flanking the kan-RAM of pACD4K-C-loxP. The substituted nucleotide is shaded. The underlined sequence base-pairs to form the stem of the stem-loop structure.

DETAILED DESCRIPTION OF THE PREFERRED EMBODIMENTS

Figure 1:
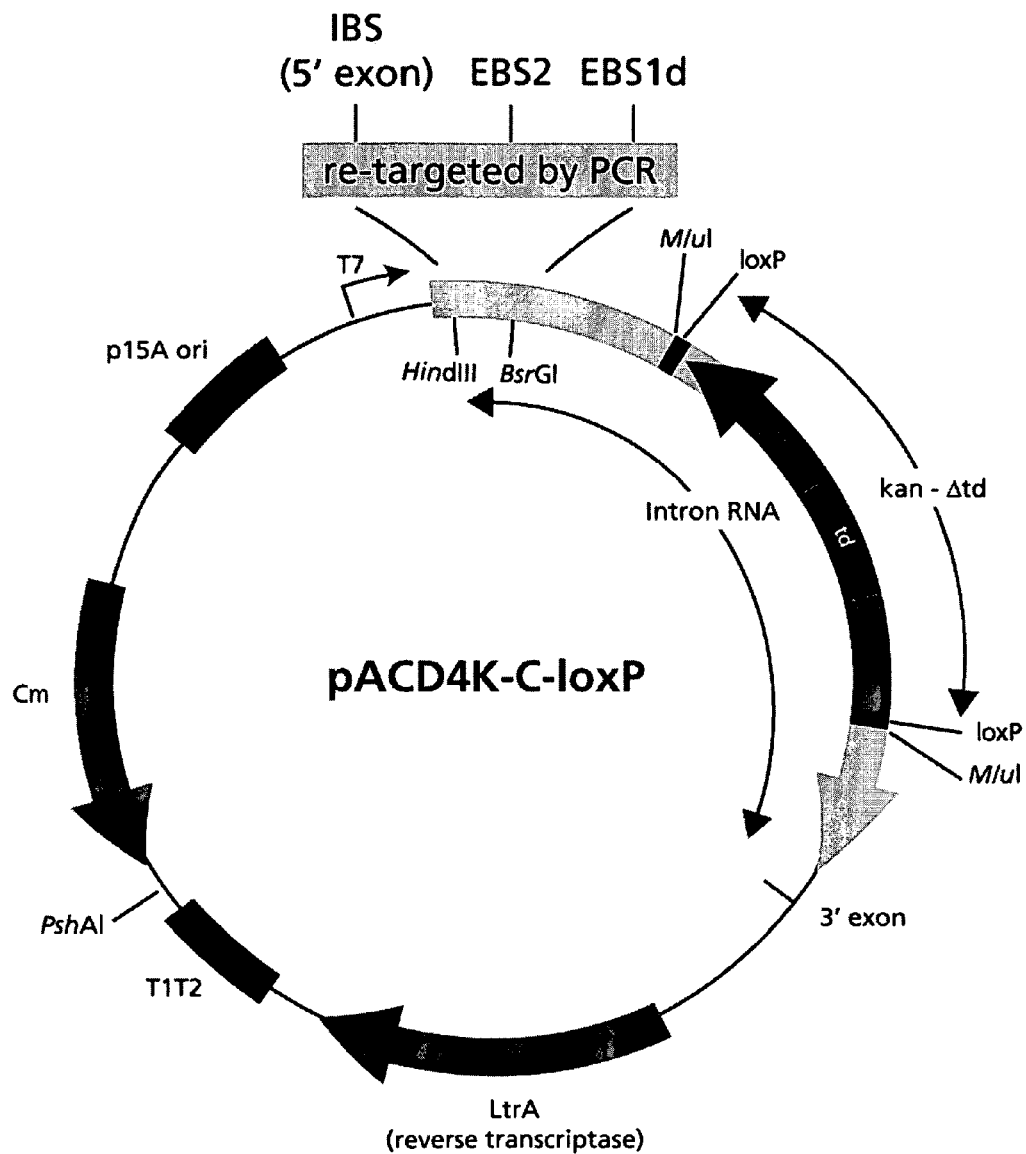
FIG. 1 depicts a schematic illustrating features of the plasmid vector, pACD4K-C-loxP. The vector comprises sequence encoding the Ll.LtrB group II intron, with the intron-encoded protein (LtrA) sequence located downstream of the 3' exon. The Ll.LtrB intron contains a kan-RAM flanked on each end by a loxP recombination site. The recombination site at the 5' end is SEQ ID NO:2 and the recombination site at the 3' end is SEQ ID NO:1.

It has been discovered that a region of a nucleic acid sequence may be selectively deleted with a site-specific recombinase system by using a retroelement to place recombination sites at targeted locations in the nucleic acid sequence. The present invention provides methods and nucleic acid constructs for targeting the recombination sites to specific locations and deleting the region between the recombination sites.

Nucleic Acid Constructs

One aspect of the invention provides nucleic acid constructs for use in placing recombination sites at targeted locations in a nucleic acid sequence. The nucleic acid constructs comprise sequence encoding a retargeting retroelement, in which at least one recombination site is carried within the retroelement sequence. The retargeting retroelement may further comprise a retrotransposition-activated selectable marker.

(a) Retroelement

A variety of retroelements are suitable for use in the invention. In general, retroelements are mobile genetic elements that code for reverse transcriptase. Hence, integration of the element is mediated by an RNA intermediate. Generally, retroelements insert at specific sequences, but they may be retargeted to other sequences using methods known to those skilled in the art. Examples of retroelements that may be used in this invention include retroviruses, retrotransposons, and mobile group II introns. In one embodiment, the retroelement is a retrotransposon selected from the group including long terminal repeat (LTR) retrotransposons and non-LTR retrotransposons. Suitable examples of LTR-containing retrotransposons include Copia and gypsy from *Drosophila melanogaster* or the Ty elements from *Saccharomyces cerevisiae*. Examples of non-LTR retrotransposons include the long interspersed elements (LINEs) and the short interspersed elements (SINEs) from eukaryotes. Suitable examples of LINEs include L1 from mammals and R2Bm from silkworm.

In a preferred embodiment, the retroelement is a mobile group II intron. In general, group II introns are self-splicing RNAs found in bacterial and archaeal genomes and in the organelles of some eukaryotes (e.g., yeast and plants). Some group II introns, however, have intron-encoded proteins that enable the introns to insert into defined sites at high efficiencies by a process called retrohoming. Retrohoming is catalyzed by a ribonucleoprotein (RNP) complex comprising the excised intron lariat RNA and an intron-encoded protein (Zimmerly et al. 1995, Cell 82, 545-554; Zimmerly et al. 1995, Cell 83, 529-538; Yang et al., 1996, Nature 381, 332-335; Guo et al. 1997, EMBO J. 16, 6835-6848). Examples of mobile group II introns that may be used in this invention include, but are not limited to, the al5.gamma, bl1, al1 and al2 introns from the mitochondria of *Saccharomyces cerevisiae*, the CoxI intron from *Podospora anserina*, and the Ll.LtrB intron from *Lactococcus lactis*. Group II introns may be retargeted to different DNA sites by altering the nucleotides in the regions of the intron that interact with the DNA (Guo et al, 2000, Science 289, 452-457; Karberg et al. 2001, Nature Biotechnology 19,1162-1167). In an exemplary embodiment, the retroelement is the retargeting *L. lactis* Ll.LtrB group II intron. (See U.S. Pat. Nos. 5,698,421; 5,804,418; 5,869,634; 6,027,895; 6,001,608; and 6,306,596, which are hereby incorporated by reference in their entirety.) In this retargeting Ll.LtrB intron, the intron-encoded protein (IEP) sequence in deleted from the intron sequence and is provided in trans. Because this retargeting Ll.LtrB intron lacks the intron-encoded protein (ΔIEP), it is unable to splice itself out of the sequence into it inserts, and the insertion is stable.

(b) Retrotransposition-activated Selectable Marker

The retroelement may further comprise a selectable marker. Generally speaking, a selectable marker encodes a product that the host cell cannot make, such that the cell acquires resistance to a specific compound or is able to survive under specific conditions. For example, the marker may code for an antibiotic resistance factor. Suitable examples of antibiotic resistance markers include, but are not limited to, those coding for proteins that impart resistance to kanamycin, spectomycin, neomycin, geneticin (G418), ampicillin, tetracycline, and chlorampenicol. The selectable marker may code for proteins that confer resistance to herbicides, such as chlorsulfuron or phosphinotricin acetyltransferase. Other appropriate selectable markers include the thymidine kinase (tk) and the adenine phosphoribosyltransferase (apr) genes, which enable selection in tk⁻ and apr⁻ cells, respectively, and the dihydrofloate reductase (dhfr) genes that confer resistance to methotrexate or trimethoprim. In one embodiment, the retroelement is the retargeting Ll.LtrB group II intron, in which a selectable marker gene is inserted into the ΔIEP region of the intron (Zhong et al. 2003, Nucleic Acids Research 31, 1656-1664). In another embodiment, the spectomycin resistance gene sequence is inserted into the retargeting Ll.LtrB intron sequence. In a preferred embodiment, the kanamycin resistance (kan$^r$) gene sequence is inserted into the retargeting Ll.LtrB intron sequence.

The selectable marker may further comprise means for selection after integration of the retroelement. Such a marker is called a retrotransposition-activated selectable marker (RAM). As an example, the selectable marker may be interrupted by a self-splicing group I intron. Thus, during group II intron retrotransposition via an RNA intermediate, the group I intron is spliced out, the selectable marker is activated, and the marker may be selected for after DNA integration. Suitable examples of group I introns that may be used in a RAM include the td and nrdB introns from bacteriophage T4, rRNA gene introns from *Tetrahymena thermophila*, *Neurospora*

*crassa*, and *Chlamydomonas reinhardtrii*, and the cytb and oxi3 introns from *Neurospora crassa*. In one embodiment, the RAM comprises an antibiotic resistance gene that is interrupted by the phage T4 td group I intron. In another embodiment, the RAM comprises a spectomycin resistance gene interrupted by the td group I intron. In a preferred embodiment, the RAM comprises a kanamycin resistance gene interrupted by the td group I intron (kan-RAM) (Ichiyanagi et al. 2002, Mol. Microbiol. 46, 1259-1272; Coros et al. 2005, Mol. Microbiol. 56, 509-524).

(c) Site-specific Recombination Sequence

The retroelement within the nucleic acid construct further comprises at least one site-specific recombination sequence. A variety of site-specific recombination systems may be used in this invention. Typically, the recombinase protein of a site-specific recombination system catalyzes recombination between two recombination sites, which are generally short stretches of DNA with identical or nearly identical sequences. Suitable examples of site-specific recombination systems include the Flp/FRT system from *Schizosaccharomyces cerevisiae*, the Cre/loxP system from *E. coli* bacteriophage P1, the RIRS system from *Zygosaccharomyces rouxii*, the φC31/attB,attP system from *Streptomyces* phage phiC31, and the mutant Gin/gix system from enteric bacteriophage Mu. Thus, suitable examples of specific recombination sites for use in the nucleic acid construct of this invention include the FRT site, the loxP site, the RS site, the attB/attP sites, and the gix site. In one embodiment the retroelement carries at least one FRT recombination site. In an alternative embodiment the retroelement carries at least one loxP recombination site.

The retroelement may carry more than one recombination site. In one embodiment, the retroelement is a group II intron further comprising a RAM, with the RAM flanked on each end by a recombination site. In another embodiment, the RAM in the group II intron is flanked on each end by a wildtype or a mutant loxP site. In a preferred embodiment, the group II intron is the retargeting *L. lactis* Ll.LtrB intron, the intron further comprising a kan-RAM, with the kan-RAM flanked on each end by a wildtype or a mutant loxP site. In an exemplary embodiment, the retroelement is the retargeting *L. lactis* Ll.LtrB group II intron, the intron further comprising a kan-RAM, with the kan-RAM flanked by SEQ ID NO:2 at the 5' end and by SEQ ID NO:1 at the 3' end (see FIGS. 1 and 3). In these last three embodiments, the region between the recombination sites may be deleted by the activity of Cre recombinase.

It is especially preferred that loxP sites flank the kan-RAM of the retargeting *L. lactis* Ll.LtrB intron. It was discovered that upon insertion of loxP sites, the Ll.LtrB intron retained sufficient mobility to allow efficient retargeting to various chromosomal locations (e.g., lacZ, betT, cynS, as demonstrated in the examples herein). In contrast, no intron mobility was observed when FRT sites flanked the kan-RAM.

(d) Other Features of the Nucleic Acid Constructs

In general, the nucleic acid constructs of the invention are engineered to carry the retroelement and the specific recombination site(s) to the host nucleic acid sequence. As appreciated by a skilled artisan, the nature of the nucleic acid construct can and will vary depending upon the origin of the nucleic acid sequence to be targeted. The nucleic acid construct may be linear or circular, may be single-stranded or double-stranded, and may be DNA, RNA, or any modification or combination thereof. The nucleic acid construct may be a phage vector, a phagemid vector, a virus vector, a baculovirus vector, a plasmid vector, a cosmid vector, a BAC vector, or a YAC vector. In one embodiment the nucleic acid construct is linear virus vector. In another embodiment, the nucleic acid construct is a circular plasmid vector. The type of plasmid vector can and will vary depending on the source of the nucleic acid sequence. For example, different plasmid vectors are generally used to target nucleic acid sequences in bacteria, yeast, fruit fly, nematode, plants, mouse, or human. In one embodiment, the plasmid vector is an *E. coli* plasmid vector, such as those based upon or derived from pBR322, pUC18/19, pACYC184, pET, or pKK plasmid vectors. (For additional vectors and more information, see Casali and Preston, *E. coli* Plasmid Vectors: Methods and Applications, 2003, Humana Press.) In a preferred embodiment, the plasmid vector is a bacterial plasmid vector derived from a pACYC184 vector.

The nucleic acid construct of the invention may further comprise a promoter to drive expression of the retroelement carrying the recombination site(s). The promoter may be constitutive or inducible. In a preferred embodiment, the promoter is an inducible promoter. Suitable examples of inducible promoters include, but are not limited to, those induced by expression of an exogenous protein (e.g., T7 RNA polymerase, SP6 RNA polymerase), presence of a small molecule (e.g., IPTG, galactose, tetracycline, steroid hormone, abscisic acid), metals (e.g., copper, zinc, cadmium), and environmental factors (e.g., heat, cold, stress).

The nucleic acid construct of the invention may further comprise a selectable marker for selection and propagation of the construct. Suitable examples of selectable markers are presented above. In one embodiment, the nucleic acid construct is a plasmid vector containing a marker that confers resistance to the antibiotic, geneticin. In another embodiment, the plasmid vector carries a chloramphenicol resistance marker.

In addition to the retroelement sequence and the recombination site sequence, the nucleic acid constructs of the invention may optionally include any the features detailed above. In an exemplary embodiment, the nucleic acid construct is a plasmid vector comprising sequence encoding the retargeting *L. lactis* Ll.LtrB intron, a kan-RAM inserted into the intron sequence, SEQ ID NO:2 at the 5' end and SEQ ID NO:1 at the 3' end of the kan-RAM, a promoter to drive expression of the intron and the intron-encoded protein, transcriptional terminators, an origin of replication, and a selectable marker for selection of the plasmid (see FIG. 1). The promoter included in the plasmid can and will vary, but a preferred one is the T7 promoter. The plasmid selectable marker can and will vary, but a preferred one is the chloramphenicol resistance gene.

Methods for Deleting a Region of a Nucleic Acid Sequence

Another aspect of the invention provides methods for deleting a targeted region of a nucleic acid sequence. Recombination sites may be placed at a targeted location in a nucleic acid sequence by using the nucleic acid constructs of this invention. One or more recombination sites may be placed in one or more targeted locations in a nucleic acid sequence, as detailed below. The region between the recombination sites may be deleted with a site-specific recombination system by providing the appropriate recombinase. As is known to one skilled in the art, the combination of recombination site and recombinase must match, i.e., they typically must be from the same site-specific recombination system. For example, Flp recombinase recognizes FRT recombination sites; Cre recombinase recognizes loxP recombination sites; R recombinase recognizes RS recombination sites; φC31 integrase recognizes attB and attP recombination sites; and mutant Gin recombinase recognizes gix recombination sites.

Retroelements may be used to place at least one recombination site at a targeted location. As detailed in Example 1, insertion of two loxP recombination sites into the retargeting

*L. lactis* Ll.LtrB group II intron did not alter the targeting ability of the group II intron. In this example, the loxP recombination sites flank the kan-RAM. When recombination sites flank a selectable marker, the selectable marker may be deleted upon expression of the appropriate recombinase (Zhong et al. 2003, Nuc. Acids Res. 31, 1656-1664). In the above-mentioned example, the kanamycin resistance gene, which was flanked by loxP sites, was deleted upon Cre expression, resulting in sensitivity to kanamycin (see Example 2).

Another aspect of the invention entails placing recombination sites at distant locations in a nucleic acid sequence and deleting the intervening region between the distant locations with a site-specific recombination system. Typically, at least one recombination site is targeted to a first location using a first nucleic acid construct of the invention, and at least one recombination site is targeted to a second location using a second nucleic acid construct of the invention. The region between the recombination sites at the first and second targeted locations may be deleted upon expression of the appropriate recombinase. As is known by a skilled artisan, the recombination sites generally must be inserted in the proper orientation in the nucleic acid sequence in order for the intervening sequence to be deleted by the recombinase.

In one embodiment, recombination sites may be placed at a first targeted location using a nucleic acid construct comprising a first retargeted retroelement carrying a RAM flanked on each end by a recombination site. Successful insertion of the first retroelement (with the RAM and recombination sites) may be confirmed by selection for the marker in the RAM. Then, the selectable marker at the first targeted location may be deleted by activity of the appropriate recombinase. Successful deletion of the selectable marker may be confirmed by sensitivity to the marker, or other methods generally known in the art. Subsequently, recombination sites may be placed at a second targeted location using a second retargeted retroelement carrying the same RAM flanked on each end by a recombination site. Again, successful insertion of the retroelement (with the RAM and recombination sites) may be confirmed by selection for the marker in the RAM. The nucleic acid sequence ideally contains three recombination sites, one at the first targeted location and two flanking the RAM at the second targeted location. Then, the region between the recombination site at the first targeted location and the appropriate recombination site at the second targeted location may be deleted by activity of the appropriate recombinase. Alternatively, recombinase activity may delete only the selectable marker at the second targeted location. As demonstrated in Example 3, however, both the intervening sequence between the first and second targeted locations and the selectable marker at the second targeted location were deleted, with nearly 100% efficiency. The successful deletion may be verified by sensitivity to the marker, as well as PCR amplifications, sequencing reactions, or other well-known methods.

In an exemplary embodiment, a first retargeted Ll.LtrB group II intron comprising a kan-RAM flanked by SEQ ID NO:2 at the 5' end and SEQ ID NO:1 at the 3' end is used to place recombination sites at a first targeted location in a nucleic acid sequence. The kan$^r$ marker at the first targeted location is deleted by expression of Cre recombinase. A second retargeted Ll.LtrB group II intron comprising a kan-RAM flanked by SEQ ID NO:2 at the 5' end and SEQ ID NO:1 at the 3' end is used to place recombination sites at a second targeted location in the nucleic acid sequence. The region between the recombination sites at the first and second targeted locations is deleted upon expression of Cre recombinase, as demonstrated in Examples 3 and 4.

In another embodiment, a first recombination site may be placed at a first targeted location using a first retargeted retroelement carrying a first RAM and a recombination site. A second recombination site may be placed at a second targeted location using a second retargeted retroelement carrying a second RAM and recombination site. Successful insertion of the retroelements at the first and second targeted locations may be verified by selection for the two different selectable markers in the first and second RAMs. The region between the recombination sites at first and second targeted locations may be deleted by activity of the appropriate recombinase.

In yet an alternative embodiment, the use of selectable markers in the retargeting retroelement may not be desired. For this, a first recombination site may be placed at a first targeted location using a first retargeted retroelement carrying a recombination site. A second recombination site may be placed at a second targeted location using a second retargeted retroelement carrying a recombination site. The region between the recombination sites at first and second targeted locations may be deleted by activity of the appropriate recombinase.

The size of the region deleted can and will vary depending upon the source of the nucleic acid sequence and the rationale for the deletion. The region selectively deleted from the nucleic acid sequence may range from about 0.1 kb to about 100 Mb in length. "Selective deletion" refers to the ability to "selectively" place recombination sites at preferred locations in a nucleic acid sequence and to "selectively" delete the region between the recombination sites. As an example, the 34 kb region between the betT gene and the lacZ gene in *E. coli* was selectively deleted using the methods of this invention (see Example 4). In another embodiment, the region selectively deleted may range from about 10 kb to about 1,000 kb in length. In another embodiment, the region selectively deleted may be about 500 kb in length. In yet another embodiment, the region selectively deleted may be about 200 kb in length. In a further embodiment, the region selectively deleted may be about 50 kb in length.

Typically, the targeted nucleic acid sequence is a DNA sequence that may contain genes, portions of genes, introns, coding sequences, control regions, intergenic regions, and non-coding sequences. The targeted nucleic acid sequence may comprise one or more chromosomes, the chromosome selected from the group consisting of bacteria, yeast, flies, worms, fish, plants, mice, and humans. In one embodiment, the targeted nucleic acid sequence is chromosomal DNA from humans. In another embodiment, the targeted nucleic acid sequence is chromosomal DNA from mice. In another embodiment, the targeted nucleic acid sequence is bacterial in origin, the bacteria selected from the group consisting of *Escherichia coli, Staphylococcus aureus, Pseudomonas aeruginosa, Salmonella enterica, Mycobacterium tuberculosis, Salmonella typhimurium, Bacillus subtilis, Helicobacter pylon, Streptococcus pneumoniae, Haemophilus influenzae, Streptococcus pyogenes, Chlamydia trachomatis, Listeria monocytogenes, Mycobacterium bovis, Enterococcus faecalis, Vibrio cholerae, Neisseria meningitides, Clostridium perfringens, Staphylococcus epidermidis, Streptococcus mutans, Bacillus anthracis, Borrelia burgdorferi, Lactococcus lactis, Serratia marcescens*, and *Shigella flexneri*. In a preferred embodiment, the targeted nucleic acid sequence is from *E. coli*. In a further embodiment, the targeted nucleic acid sequence is from *Staphylococcus aureus*. In yet another embodiment, the targeted nucleic acid sequence is from *Clostridium perfringens*.

Kits for Deleting a Region of a Nucleic Acid Sequence

A further aspect of the invention encompasses a kit for selectively deleting a region of a nucleic acid sequence. Minimally, the kit comprises a nucleic acid construct of the invention, as described above, instructions for targeting and inserting recombination sites at preferred locations in the nucleic acid sequence, and instructions for deleting the region between the recombination sites. In a preferred embodiment, the nucleic acid construct comprises the retargeting Ll.LtrB group II intron carrying a kan-RAM, the kan-RAM flanked by SEQ ID NO:2 at the 5' end and SEQ ID NO:1 at the 3' end, and the group II intron under control of an inducible T7 promoter. The kit may further comprise means to retarget the Ll.LtrB group II intron to a specific location in a nucleic acid sequence. In an additional embodiment, the kit may further comprise means to express Cre recombinase.

Definitions

The terms "retargeted" and "retargeting" used herein refer to the ability to modify retroelements such that they will target and insert at different locations in a DNA sequence. In the case of group II introns, the nucleotides in the regions of the intron that interact with the DNA can be altered by PCR such that the group II intron will target to specific locations.

A "retroelement" is a type of a transposable element that can move to different positions in a nucleic acid sequence; hence they are called mobile elements. Retroelements are unique in that they code for reverse transcriptase. A retroelement moves by first being transcribed into an RNA copy that is then reconverted into DNA by its reverse transcriptase, and then the DNA is inserted somewhere else within the sequence. Retroviruses, retrotransposons, and mobile group II introns are examples of retroelements. While retroelements are types of transposable elements, not all transposable elements are retroelements. In particular, transposons are not retroelements.

The terms "selective deletion" or "selectively deleting" used herein refer to the ability to control or select what region of the nucleic acid sequence is to be deleted. The ability to select the region is conferred by the use of retargeting retroelements to place recombination sites at specific, desired locations in a nucleic acid sequence. Once the recombination sites are placed at the desired locations, the region between them may be deleted by activity of the appropriate recombinase. Thus, specific regions of a nucleic acid sequence may be targeted and deleted.

The terms "targeted" and "targeting" used herein refer to the inherent mature of retroelements to move to and insert at a specific nucleotide sequence.

As various changes could be made in the above constructs and methods without departing from the scope of the invention, it is intended that all matter contained in the above description and in the examples given below, shall be interpreted as illustrative and not in a limiting sense.

EXAMPLES

The following examples illustrate various embodiments of the invention.

Example 1

Disruption of the lacZ Gene in *E. coli*

The lacZ gene was targeted for disruption using the TargeTron pACD4K-C-loxP vector (FIG. 1). This vector comprises sequence coding for the Ll.LtrB group II intron RNA and intron-encoded protein. A kanamycin retrotransposon-activated selectable marker (kan-RAM) is inserted into the intron RNA sequence. The open reading frame of the $kan^r$ gene is interrupted by the td group I intron, which is spliced out upon expression of the intron RNA. After removal of the group I intron, the $kan^r$ gene is still expressed as a reverse complement within the intron RNA, preventing $kan^r$ gene expression (e.g. translation of the 3'5'-aminoglycoside phosphotransferase). Upon insertion of the intron into the genome, the reverse complement of the intron is synthesized and kanamycin resistance is activated. The kan-RAM sequence in the plasmid vector is flanked on each end by a loxP recombination site.

Target site design and intron re-targeting. Plasmid pACD4K-C-loxP (Sigma, T2826) was created by linearizing plasmid pACD4-C (Perutka et al. 2004, J. Molecular Biology 336: 421-439) at the MluI site and inserting a PCR generated fragment containing the kan-RAM of pACD4K-C with primer-inserted loxP sites at each end. *Escherichia coli* BL21(DE3)-T1$^R$ (Sigma, B2935) was used in all knockout experiments. In some cases, *E. coli* GC5 (Sigma, G3169) was used to purify, clone, and prep re-targeted plasmids prior to knockout experiments in BL21(DE3). For selections, kanamycin was included in LB-plates at 25 µg/ml (Teknova, L1023).

Three gene-specific primers were designed to re-target the intron to the 1063|1064a position of the lacZ gene. The sequences of the primers, as well as the lacZ 1063|1064a target site are shown in Table 1. (The letters "a" and "s" refer to sense and antisense orientation of the intron within the ORF. The underlined portions of the PCR primers are variable depending on gene specific targeting.) The EBS1d and EBS2 primers are used to mutate the EBS loops in the intron RNA that interact directly with the chromosomal target site DNA via base pairing. The IBS primer is used to mutate the intron to preserve EBS-IBS base pairing required for intron splicing prior to target site insertion. These three primers were used, along a fourth invariable primer, EBS universal, to mutate the region of plasmid DNA that encodes the intron RNA (performed as described in the User Guide for the TargeTron Gene Knockout System, Sigma Cat. No. TA0100). The 350 bp re-targeted fragment was ligated into pACD4K-C-loxP at the HindIII and BsrGI sites. The re-targeted plasmid was introduced BL21(DE3) cells using standard procedures.

TABLE 1

Target site and primers for the lacZ gene.

| | | SEQ ID NO |
|---|---|---|
| lacZ gene target site | | |
| lacZ 1063|1064a | CATGCAGAGGATGATGCTCGTGACGGTTAA-intron-CGCCTCGAATCAGCA | 3 |
| Re-targeting primers for the lacZ 1063/1064a target site | | |
| lacZ IBS | AAAAAAGCTTATAATTATCCTTA<u>CGTGAC</u>G<u>GTTA</u>AGTGCGCCCAGATAGGGTG | 4 |
| lacZ EBS1d | CAGATTGTACAAATGTGGTGATAACAGATAAGTC<u>GGTTAAC</u>GTAACTTACCTTTCTTTGT | 5 |

TABLE 1-continued

Target site and primers for the lacZ gene.

| | | SEQ ID NO |
|---|---|---|
| lacZ EBS2 | TGAACGCAAGTTTCTAATTTCGGTTTCACGTCGA TAGAGGAAAGTGTCT | 6 |
| EBS Universal | CGAAATTAGAAACTTGCGTTCAGTAAAC | 7 |

Primers for detection of chromosomal insertions in the lacZ gene

| 3p-exon-1 | TACGCAGCGGTATTTTCGATCAG | 8 |
|---|---|---|
| lacZ-F | CTGTGGAGCGCCGAAATCCCGAAT | 9 |
| lacZ-R | ATCCACCACATACAGGCCGTAGCG | 10 |

Induction of RNP expression for insertional gene knockout. Transformed BL21 (DE3) strains were grown overnight in 2 ml of LB with 1% glucose and 25 µg/ml chloramphenicol. Glucose was added when culturing pACD4K-C plasmids with DE3 strains to keep the lacUV5 promoter for the T7 RNA polymerase gene repressed during growth of starter cultures. This prevents premature group II intron transcription before IPTG induction that may have an adverse effect on viability. After overnight growth the culture was diluted 1:50 in 2 ml of LB with 1% glucose and 25 µg/ml chloramphenicol and grown at 37° C. to an $OD_{600}$ of approximately 0.2. IPTG was added to a final concentration of 500 µM for induction of group II intron transcription. Cultures were incubated at 30° C. for 30 minutes and then spun down at 6000 rpm for 1 minute. The supernatants were discarded and the pellets were resuspended in LB with 1% glucose, no chloramphenicol, and grown at 30° C. for one hour. After rescue growth in LB with 1% glucose at 30° C. with no antibiotic, the cultures were spun down again at 6000 rpm for 1 minute and resuspended in 1 ml of LB. 100 µl of this resuspended culture was plated on LB plus kanamycin 25 µg/ml plates for selection of group II intron insertion. Growth on kanamycin plates at 50 µg/ml was found to produce fewer to no colonies.

Confirmation of knockouts by colony PCR. Once retrotransposition via an RNA intermediate has occurred, the td group I intron is spliced out thereby activating the $kan^r$ marker that is then selected for after the intron has integrated into a DNA target site. Kanamycin plates were incubated overnight at 30° C. or at room temperature for several days. Detection of insertions was performed by using either two gene specific primers spanning the target site (e.g. lacZ-F/R, Table 1) or by using a gene specific primer and a group II intron primer (e.g. lacZ-F and 3p-exon-1, Table 1). Gene specific primers were chosen at a distance of ~150 bp from the insertion site and used together with intron specific primer 3p-exon-1 that binds within the kan-RAM. Positive colony PCR results were then purified using the GenElute™ PCR Clean-up Kit (Sigma Cat. No. NA1020) and submitted for sequencing.

Figure 2D:
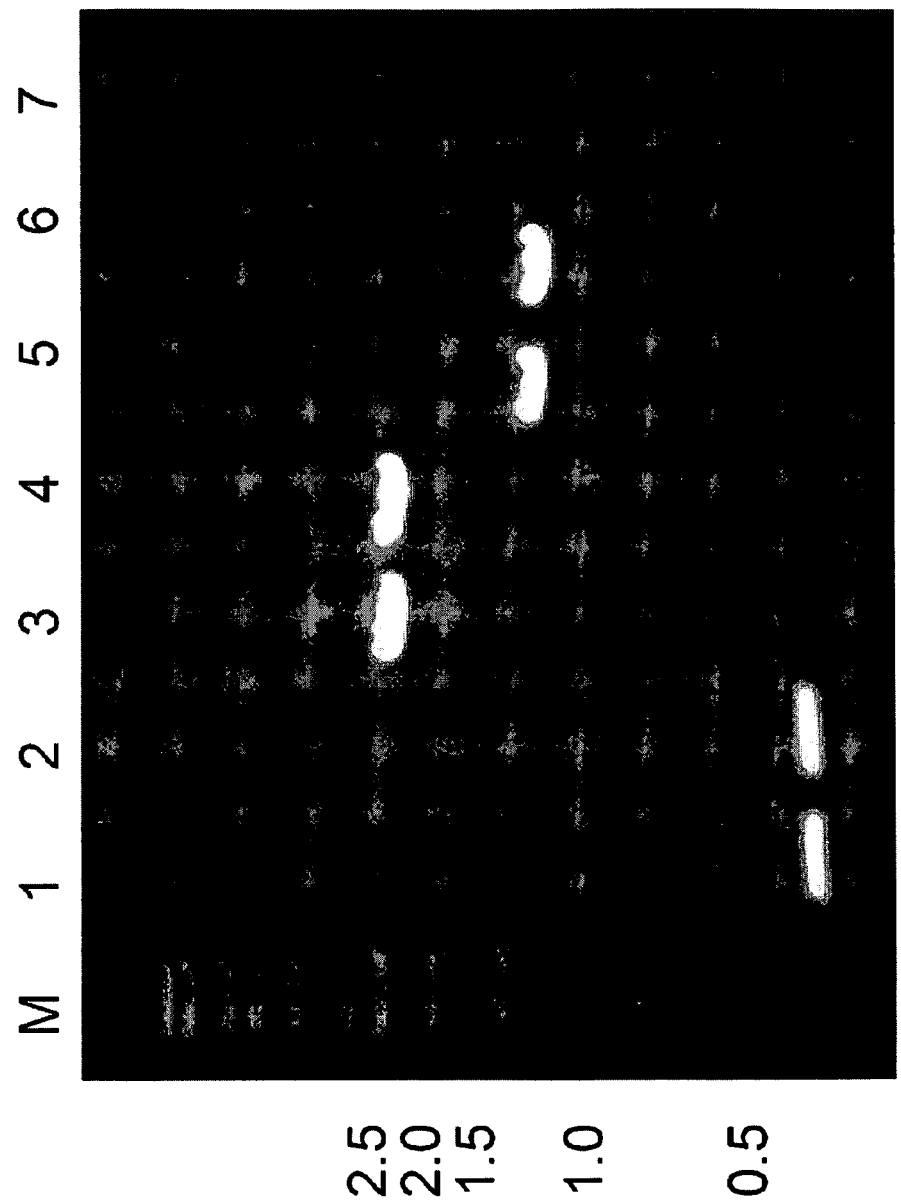
FIG. 2 illustrates deletion of the kanamycin marker from the targeted lacZ gene. Panels A-C present schematics of the E. coli chromosome and panel D presents an image of a gel with PCR products. Panel A illustrates the insertion of the group II intron into the lacZ target gene (black lines). The kanamycin marker (dark gray) within the intron is flanked by directly repeated loxP sites (stem loop structures). The lacZ gene specific primers used for PCR are represented by small black arrows above and below the lacZ gene. Panel B illustrates, that upon expression of Cre recombinase in the lacZ knockout strain, Cre binds and cuts the loxP stem loops (blank spaces in the loops). Panel C shows that Cre-loxP site-specific recombination results in the excision of the kanamycin marker leaving behind a single loxP scar in the chromosome. Panel D displays the results of PCR using the lacZ gene specific primers. The 336 bp amplicon in lanes 1 and 2 was amplified from w.t. BL21 cells. The 2.3 kb amplicon in lanes 3 and 4 was amplified in the lacZ::intron disruption strain (diagrammed in panel A). The 1.3 kb amplicon in lanes 5 and 6 represents the shortened intron after kanamycin removal by Cre/loxP recombination (diagrammed in panel C). Lane 7 is a no template PCR control. Lane M is a 1 kb DNA ladder ranging from 0.5 to 10 kb.

The lacZ gene was disrupted by targeted insertion of the group II intron (FIG. 2A). Using lacZ gene specific primers, a 336 bp amplicon was amplified from wild type cells, whereas a 2.3 kb amplicon was amplified from lacZ 1063|1064a kan-loxP knockout cells (FIG. 2D, lanes 1-4). Thus, flanking the kan-RAM marker with loxP sequences did not significantly alter the activity of the intron to target the lacZ 1063|1064a insertion site. In contrast, flanking the kan-RAM with FRT sites resulted in a dramatic decrease (>100-fold) in the yield of $kan^r$ colonies when targeting the lacZ gene at the 1063|1064a position. During cloning experiments to place loxP sites on either side of the kan-RAM marker, a deletion-substitution mutation was found in the 5' loxP site (FIG. 3), but not the 3' loxP site. This mutation reduces the continuous loxP stem-loop size from 13 to 10 bp. This deletion had no significant effect on the ability to target the lacZ 1063|1064a position. When the mutation in the 5' loxP site was repaired, however, the gene targeting efficiency of the lacZ 1063'1064a position dropped approximately 5-fold.

Example 2

Removal of Chromosomal Kanamycin Markers via Cre/loxP Recombination

Often it is desirable to remove inserted antibiotic markers from the chromosome to allow for additional knockouts or use of the marker on plasmids in the knockout strain. The $kan^r$ marker in the lacZ::intron kan-loxP knockout cells can be excised by expression of Cre recombinase. Cre recombinase acts on the loxP sites to catalyze the excision of the intervening DNA between the sites while leaving one loxP site behind (FIGS. 2B and C).

The lacZ 1063|1064a kan-loxP knockout strain was generated as described above. The donor plasmid was cured by overnight growth in LB containing 500 µM IPTG and screened for a chloramphenicol sensitive isolate. This strain was then made competent and transformed using the reagents and procedures in the RAPIDTRANSIT™ Transformation Kit (Sigma Cat. No. R2653). About 5-10 ng of Cre-705;cm plasmid (GeneBridges Cat. No A112) was added to 100 µl aliquots of the lacZ 1063|1064a kan-loxP competent cells and incubated on ice for 10 min. The cells were heat shocked at 42° C. for 45 seconds followed by a 2-minute incubation on ice. Then 900 µl of pre-warmed recovery media was added and the cells were incubated at 30° C. for 1.5-2 hours with shaking. The entire 1.0 ml transformation reaction was centrifuged, 900 µl was removed and the pellet was resuspended in the remaining 100 µl and plated on LB plus chloramphenicol (15 µg/ml). The plates were incubated at 30° C. for 2 days. Isolated colonies were picked into 2.0 ml LB media and grown at 30° C. for 2-3 hours with shaking. The cultures were then grown overnight at 37° C. to induce expression of Cre recombinase while at the same time curing the temperature sensitive 705-Cre plasmid. To test for the efficiency of kanamycin removal, ten-fold serial dilutions of the overnight cultures were diluted to $1 \times 10^{-5}$. 100 µl of each dilution was plated on LB and LB plus kanamycin. Colony PCR was performed using the lacZ F/R gene specific primers (Table 1).

PCR confirmed removal of the kanamycin marker. Colony PCR with lacZ specific primers revealed a 1.3 kb amplicon after Cre/loxP recombination, indicating excision of the 1 kb kanamycin marker (FIG. 2D). Isolation of individual colonies grown on LB alone or LB plus kanamycin revealed that the removal of the kanamycin marker occurred at a frequency of >99%. DNA sequencing confirmed the removal of the kanamycin marker and the presence of the single loxP scar within the intron.

Example 3

Lac Operon Deletion by Site-specific Delivery of Multiple loxP Sites

Figure 4:
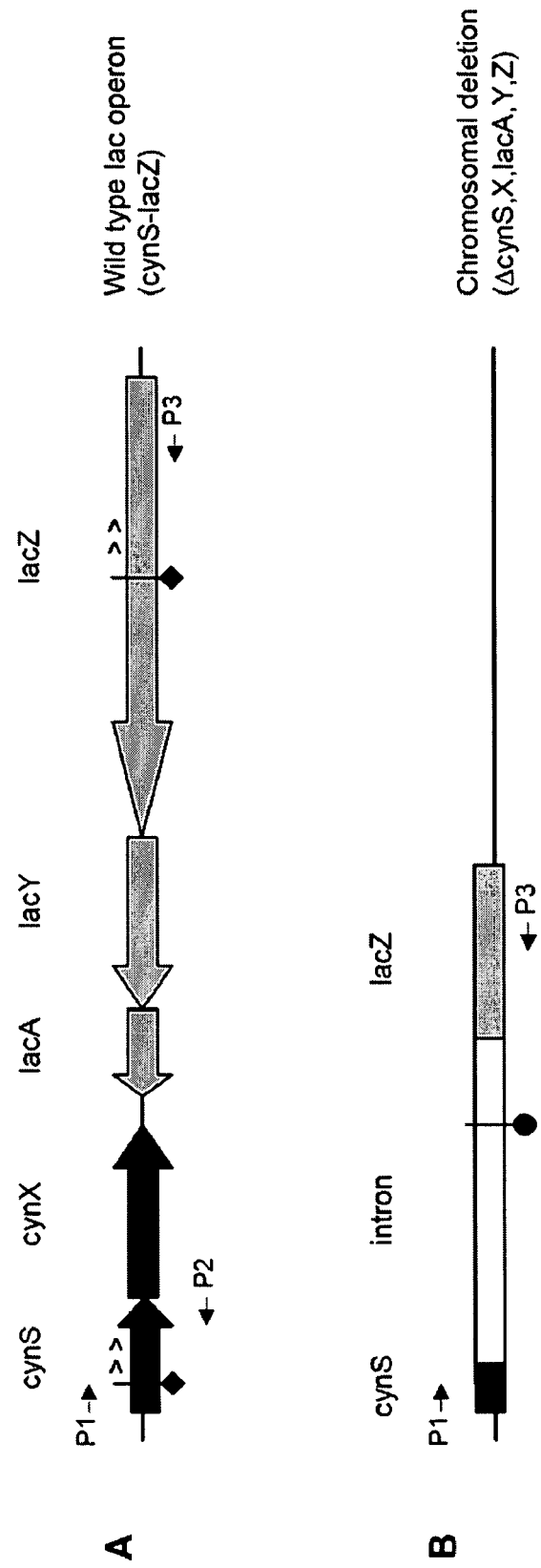
FIG. 4 illustrates targeted deletion of the lacZ operon using group II intron-mediated placement of loxP sites and Cre/loxP recombination. Panels A and B present schematics of the E. coli chromosome and panel C presents an image of a PCR gel. Panel A illustrates the wild type lac operon (large gray arrows) and the cyn operon (large black arrows). Intron insertion sites (cynS 120/121 and lacZ 1063/1064) are indicated by (♦). Small black arrows labeled P1, P2 and P3 represent forward and reverse gene specific PCR primers. All initial loxP sites are indicated by a (>). Panel B depicts the chromosomal deletion after targeted double knockout. The single loxP scar after recombination is represented by a (•). The gel in Panel C depicts colony PCR verification of the operon deletion using cynS and lacZ gene specific primers. PCR on the samples in lanes 1-4 was performed using cynS gene specific primers (P1/P2). The 475 bp amplicon in lane 1 was amplified from w.t. BL21 template. Lanes 2-3 represent duplicate reactions of an isolated colony after Cre recombination of the double knockout; no product was amplified. Lane 4 is a no template PCR control. PCR on the samples in lanes 5-8 was done using cynS/lacZ gene specific primers (P1/P3). The 5.9 kb amplicon in lane 5 was amplified from w.t. BL21 template (diagrammed in panel A). The 1.2 kb amplicons in lanes 6-7 are indicative of operon deletion (diagrammed in panel B). Lane 8 is a no template PCR control. Lane M is a PCR ladder ranging from 50 bp to 2.0 kb.
Figure 4:
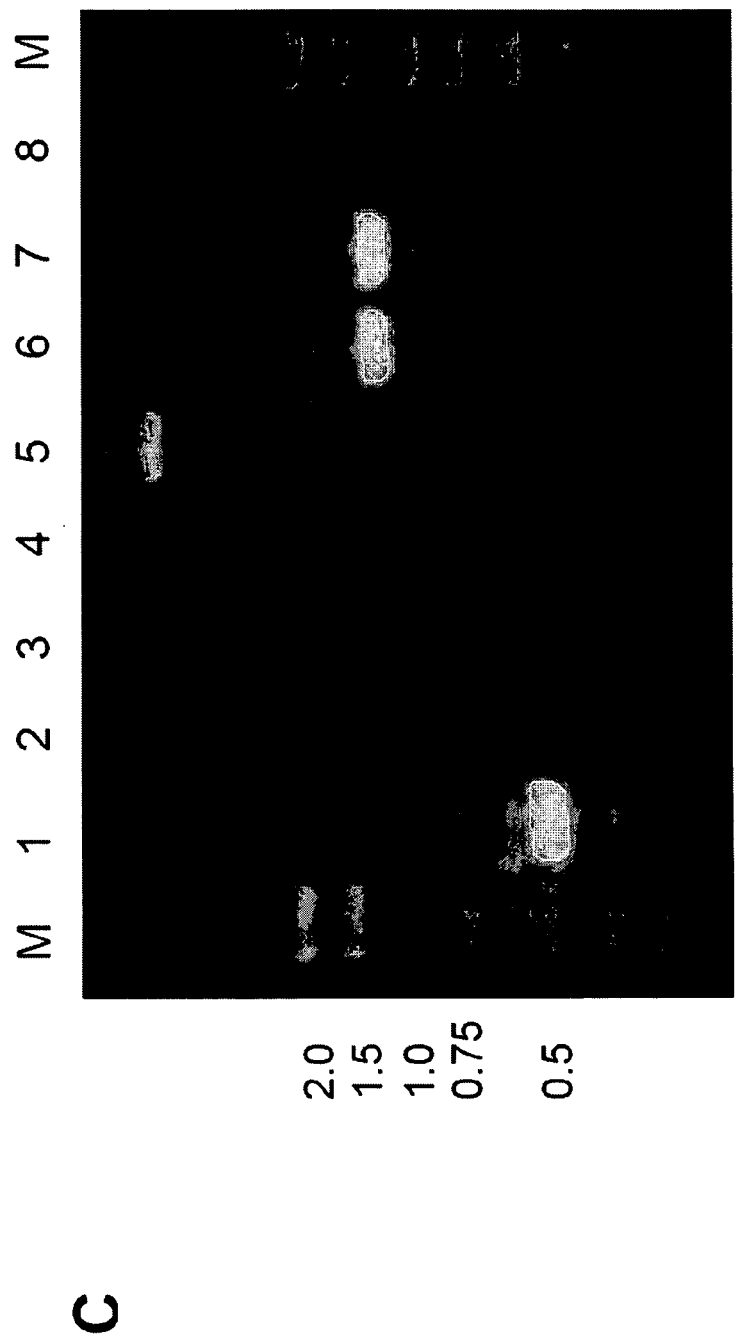

Following removal of the kan-RAM by Cre excision, an intron is left behind containing a single loxP site. If a second insertion is performed in which two new loxP sites are inserted in the same orientation as the loxP scar, chromosomal deletions should be obtained upon expression of Cre recombinase. To test this scheme, the cynS gene was targeted with a kan-loxP-RAM in a lacZ 1063|1064a-loxP scar knockout strain in an attempt to remove the majority of the lac operon (FIG. 4).

The pACD4K-C-loxP vector was re-targeted to position 120|121s of the cynS gene (Table 2) using methods described in Example 1. To generate the double knockout, the lacZ 1063|1064a-loxP scar knockout strain was made competent and transformed with the re-targeted plasmid using one of the following methods: (1) direct transformation of the ligation reaction into the knockout host, (2) transformation of the ligation reaction into a highly competent cloning strain such as GC5 (Sigma, G3169) followed by mini-prep of the entire pooled DNA, then transforming into BL21(DE3), or (3) picking of individual GC5 colonies to isolate clonal re-targeted plasmids, then transforming into BL21(DE3). Method (1) above was found to work best when BL21(DE3) transformation efficiencies were maximal (e.g. $>10^6$ cfu/µg). Method (3) is recommended as a last resort for difficult target sites in $E.$ $coli$ or as a slower, more methodical approach to be applied when experimenting with novel bacterial hosts. Double knockouts were selected on LB plus kanamycin plates. Colony PCR was performed using cynS-R with 3p-exon-1 and lacZ F/R gene specific primers (Tables 1 and 2). The cynS 120|121s donor plasmid was cured as described above. The cynS-lacZ double knockout strain was made competent and transformed with 705-Cre as described above. Expression of Cre recombinase was done as previously described. Isolated colonies were tested in colony PCR for Cre-loxP recombination using cynS-F and lacZ-F gene specific primers (Tables 1 and 2).

TABLE 2

Target site and primers for the cynS gene.

| | | SEQ ID NO |
|---|---|---|
| cynS gene target site | | |
| cynS 120\|121s | GAGATTGCCGACGGCACCGGTCTGGCAGAA-intron-GCCTTTGTAACCGCG | 11 |
| Primers for detection of chromosomal insertions in the cynS gene | | |
| 3p-exon-1 | TTACGCAGCGGTATTTTTCGATCAG | 8 |
| cynS-F | GCAATATTCGTCTTGATCTTGCCGATGC | 12 |
| cynS-R | CGTCTTTTGATGGTTGCGCATGGCTG | 13 |

The cynS 120|121s target site was efficiently disrupted with the intron-kan-loxP-RAM and knockout cells were selected on kanamycin plates, further confirming that the mobility of the intron is not affected by the loxP sequences. Upon expression of the Cre recombinase, colonies with lac operon deletions were obtained at a frequency of 100% (e.g. 12 of 12 colonies had the deletion). PCR using cynS gene specific primers revealed the presence of 475 bp amplicon in w.t. BL21 cells, whereas no fragment was amplified in the lac operon deletion strain (FIG. 4C, lanes 1-3). PCR using cynS and lacZ specific primers amplified a 5.9 kb fragment in w.t. BL21 cells and a 1.2 kb fragment in the lac operon deletion cells, indicating a 4.7 kb excision (FIG. 4C, lanes 5-7). Following insertion of the second kan-loxP-RAM, three loxP sites are present. Upon expression of Cre recombinase, it is possible that the lac operon may be deleted, but the kan-RAM marker may remain in some clones. All colonies screened showed removal of both the lac operon and the second kan-loxP-RAM in a single step of Cre expression. DNA sequencing confirmed the 4.7 kb chromosomal deletion between the cynS and lacZ target sites with the single loxP scar remaining within the intron.

Example 4

Targeted 34 kb Chromosomal Deletion

To determine whether much larger chromosomal deletions could be generated using this method, the 603|604s position in the betT gene was targeted for intron-kan-loxP-RAM insertion in a lacZ 1063|1064a-loxP scar knockout strain. The betT gene is located about 35 kb upstream of the lacZ gene in the $E.$ $coli$ chromosome. All experiments were done as described in the lac operon deletion with the following exceptions. To confirm the double knockout at lacZ 1063|1064a and betT 603|604s, colony PCR was performed using betT-R and 3p-exon-1 and lacZ F/R gene specific primers (Tables 1 and 3). After Cre-loxP recombination, colony PCR and DNA sequencing were performed using befT-F and lacZ-F gene specific primers (Tables 1 and 3).

TABLE 3

Target site and primers for the betT gene.

| | | SEQ ID NO |
|---|---|---|
| betT gene target site | | |
| betT 603\|604s | CACTCAGTGGATATTGCAGCGGTGATCGGC-intron-ACTATCTTCGGTATT | 14 |
| Primers for detection of chromosomal insertions in the betT gene | | |
| 3p-exon-1 | TACGCAGCGGTATTTTTCGATCAG | 8 |
| betT-F | TTTCACACAGCAGGGAAAAGGACAAAATC | 15 |
| betT-R | GCCATCGAATCGGGAATATCAAAC | 16 |

The betT 603|604s target site was successfully disrupted in the lacZ 1063|1064a-loxP scar knockout strain. As previously shown for the lac operon, 100% of the isolated colonies showed complete removal of the ~34 kb sequence, which contains about 28 genes, between the betT and lacZ target sites as determined by colony PCR and DNA sequencing. Due to the high efficiency of targeted insertion and Cre-loxP site-specific recombination, we suspect that the size of chromosomal deletion is limitless in regions that are not essential for cell survival.

Example 5

Cyanate Inhibits Growth of Chromosomal Deletion Strains Lacking cynS and cynT

This work has generated several $E.$ $coli$ mutants in which the cyn operon has been partially or entirely removed. The cyn operon, located just upstream of the lac operon, consists of three genes, cynT, cynS and cynX, transcribed in that order. Two of the deletion strains which are described above, ΔcynS 120|121s-lacZ1063|1064a and ΔbetT 603|604s-lacZ1063|1064a, remove cynS-X and the entire cyn operon, respectively. Another deletion strain, not previously described, was also generated in this study. The ΔcynX 1077|1078s-lacZ1063|1064a strain lacks only the cynX gene of the cyn operon. It is known that cynT and cynS are involved in the degradation of cyanate and that strains deficient of these genes are sensitive to cyanate.

To test these strains for their ability to catalyze cyanate degradation, a final concentration of 10 mM potassium cyanate (Sigma-Aldrich Cat. No. 215074) was spread onto M9 minimal salts agar plates (Teknova Cat. No. M1200). Isolated colonies for each strain were picked from LB plates, reconstituted in 20 μl of sterile water and streaked on M9 agar plates or M9 plus 10 mM potassium cyanate agar plates. The plates were incubated overnight at 37° C. under normal $CO_2$ levels (e.g. no additional $CO_2$ was provided to overcome cyanate toxicity).

Figure 5:
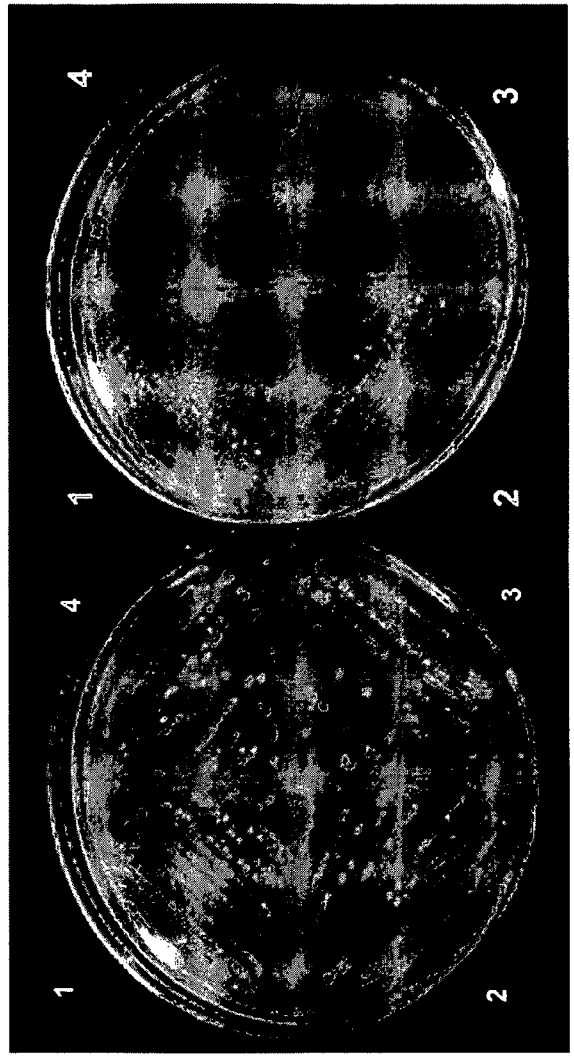
FIG. 5 illustrates the phenotype of cyn operon deletion mutants. Presented at the bottom is an image of cyn operon deletion mutants grown on plates with M9 minimal medium (left) or M9 minimal medium with 10 mM potassium cyanate (right). All mutants containing a cynS partial or complete deletion exhibited cyanate sensitivity. The table at the top identifies the strain grown in each of the quadrants on the plates.

FIG. 5 shows that both wild type *E. coli* and the deletion strain lacking only cynX grew well in the presence of 10 mM potassium cyanate, while strains lacking cynS or the entire cyn operon were sensitive to cyanate. With respect to polar effects, these data show that insertion of a group II intron into cynX within the cyn operon does not have a significant effect on the function of the other genes (cynT or cynS) located upstream. These findings also confirm that the deleted regions are not relocating to other locations around the chromosome and perhaps restoring cynS function.

What is claimed is:

1. A method for selectively deleting a region of a chromosome in a prokaryotic cell, the method comprising:
   a) providing to the prokaryotic cell a first nucleic acid encoding a first retargeted LI.LtrB intron and a first intron-encoded protein (IEP), wherein the first LI.LtrB intron and the first IEP sequences are under control of expression control sequences, wherein the first retargeted LI.LtrB intron comprises a first loxP site, and the first retargeted LI.LtrB intron inserts into a first targeted location in the chromosome;
   b) providing to the prokaryotic cell comprising the first nucleic acid, a second nucleic acid encoding a second retargeted LI.LtrB intron and a second IEP, wherein the LI.LtrB intron and the second IEP sequences are under control of expression control sequences, wherein the second retargeted LI.LtrB intron comprises a second loxP site, and the second retargeted LI.LtrB intron inserts into a second targeted location in the chromosome, wherein the first and the second loxP sites are in the same orientation; and
   c) providing to the prokaryotic cell comprising the first and the second nucleic acid a Cre recombinase that mediates recombination between the first and the second loxP sites to delete the region between the sites at the first and the second targeted locations in the chromosome of the prokaryotic cell.

2. The method of claim 1, wherein each of the first and the second retargeted LI.LtrB introns each further comprise a selectable marker flanked by a 5' end loxP site and a 3' end loxP site that are in the same orientation, wherein the 5' end and the 3' end loxP sites at first and the second targeted location are able to recombine thereby deleting the selectable marker and leaving one loxP site at each targeted location, the first loxP site at the first targeted location and the second loxP site at the second targeted location.

3. The method of claim 2, wherein the 5' end loxP site is a mutant site consisting of SEQ ID NO:2 and the 3' end loxP site is a wild-type site consisting of SEQ ID NO:1.

4. The method of claim 3, wherein each of the selectable markers is a retrotransposition-activated selectable marker (RAM).

5. The method of claim 4, wherein each RAM is a kanamycin resistance gene interrupted by a td group I intron (kan-RAM).

6. The method of claim 4, wherein the RAM at the first targeted location is removed by transient expression of the Cre recombinase prior to step (b).

7. The method of claim 2, wherein the selectable marker at the first targeted location is removed by transient expression of the Cre recombinase prior to step (b).

8. The method of claim 1, wherein the region selectively deleted from the chromosome is from about 0.1 kb to about 100 Mb in length.

9. The method of claim 1, wherein the region selectively deleted from the chromosome is from about 10 kb to about 1,000 kb in length.

10. The method of claim 1, wherein the prokaryotic cell is selected from the group consisting of *Escherichia coli, Staphylococcus aureus, Lactococcus lactis, Shigella flexneri, Salmonella typhimurium*, and *Clostridium perfringens*.

* * * * *

SEQUENCE LISTING

```
<160> NUMBER OF SEQ ID NOS: 16

<210> SEQ ID NO 1
<211> LENGTH: 34
<212> TYPE: DNA
<213> ORGANISM: Bacteriophage P1

<400> SEQUENCE: 1
ataacttcgt atagcataca ttatacgaag ttat                            34

<210> SEQ ID NO 2
<211> LENGTH: 33
<212> TYPE: DNA
<213> ORGANISM: Bacteriophage P1

<400> SEQUENCE: 2
ctacttcgta tagcatacat tatacgaagt tat                             33

<210> SEQ ID NO 3
<211> LENGTH: 45
<212> TYPE: DNA
<213> ORGANISM: Escherichia coli
<220> FEATURE:
<221> NAME/KEY: Intron
<222> LOCATION: (30)..(31)
<220> FEATURE:
<221> NAME/KEY: Intron
<222> LOCATION: (30)..(31)

<400> SEQUENCE: 3
catgcagagg atgatgctcg tgacggttaa cgcctcgaat cagca                45

<210> SEQ ID NO 4
<211> LENGTH: 53
<212> TYPE: DNA
<213> ORGANISM: Artificial
<220> FEATURE:
<223> OTHER INFORMATION: Primer

<400> SEQUENCE: 4
aaaaaagctt ataattatcc ttacgtgacg gttaagtgcg cccagatagg gtg       53

<210> SEQ ID NO 5
<211> LENGTH: 60
<212> TYPE: DNA
<213> ORGANISM: Artificial
<220> FEATURE:
<223> OTHER INFORMATION: Primer

<400> SEQUENCE: 5
```

-continued cagattgtac aaatgtggtg ataacagata agtcggttaa cgtaacttac ctttctttgt    60

<210> SEQ ID NO 6
<211> LENGTH: 49
<212> TYPE: DNA
<213> ORGANISM: Artificial
<220> FEATURE:
<223> OTHER INFORMATION: Primer

<400> SEQUENCE: 6
tgaacgcaag tttctaattt cggtttcacg tcgatagagg aaagtgtct    49

<210> SEQ ID NO 7
<211> LENGTH: 28
<212> TYPE: DNA
<213> ORGANISM: Artificial
<220> FEATURE:
<223> OTHER INFORMATION: Primer

<400> SEQUENCE: 7
cgaaattaga aacttgcgtt cagtaaac    28

<210> SEQ ID NO 8
<211> LENGTH: 24
<212> TYPE: DNA
<213> ORGANISM: Artificial
<220> FEATURE:
<223> OTHER INFORMATION: Primer

<400> SEQUENCE: 8
tacgcagcgg tattttcga tcag    24

<210> SEQ ID NO 9
<211> LENGTH: 24
<212> TYPE: DNA
<213> ORGANISM: Artificial
<220> FEATURE:
<223> OTHER INFORMATION: Primer

<400> SEQUENCE: 9
ctgtggagcg ccgaaatccc gaat    24

<210> SEQ ID NO 10
<211> LENGTH: 24
<212> TYPE: DNA
<213> ORGANISM: Artificial
<220> FEATURE:
<223> OTHER INFORMATION: Primer

<400> SEQUENCE: 10
atccaccaca tacaggccgt agcg    24

<210> SEQ ID NO 11
<211> LENGTH: 45
<212> TYPE: DNA
<213> ORGANISM: Escherichia coli
<220> FEATURE:
<221> NAME/KEY: Intron
<222> LOCATION: (30)..(31)
<220> FEATURE:
<221> NAME/KEY: Intron
<222> LOCATION: (30)..(31)

<400> SEQUENCE: 11
gagattgccg acggcaccgg tctggcagaa gcctttgtaa ccgcg    45

<210> SEQ ID NO 12

```
<211> LENGTH: 28
<212> TYPE: DNA
<213> ORGANISM: Artificial
<220> FEATURE:
<223> OTHER INFORMATION: Primer

<400> SEQUENCE: 12
gcaatattcg tcttgatctt gccgatgc                                          28

<210> SEQ ID NO 13
<211> LENGTH: 26
<212> TYPE: DNA
<213> ORGANISM: Artificial
<220> FEATURE:
<223> OTHER INFORMATION: Primer

<400> SEQUENCE: 13
cgtcttttga tggttgcgca tggctg                                            26

<210> SEQ ID NO 14
<211> LENGTH: 45
<212> TYPE: DNA
<213> ORGANISM: Escherichia coli
<220> FEATURE:
<221> NAME/KEY: Intron
<222> LOCATION: (30)..(31)
<220> FEATURE:
<221> NAME/KEY: Intron
<222> LOCATION: (30)..(31)

<400> SEQUENCE: 14
cactcagtgg atattgcagc ggtgatcggc actatcttcg gtatt                       45

<210> SEQ ID NO 15
<211> LENGTH: 29
<212> TYPE: DNA
<213> ORGANISM: Artificial
<220> FEATURE:
<223> OTHER INFORMATION: Primer

<400> SEQUENCE: 15
tttcacacag cagggaaaag gacaaaatc                                         29

<210> SEQ ID NO 16
<211> LENGTH: 24
<212> TYPE: DNA
<213> ORGANISM: Artificial
<220> FEATURE:
<223> OTHER INFORMATION: Primer

<400> SEQUENCE: 16
gccatcgaat cgggaatatc aaac                                              24
```